(12) United States Patent
Cai et al.

(10) Patent No.: US 8,978,897 B2
(45) Date of Patent: Mar. 17, 2015

(54) DISPOSABLE POLYMER-STRUCTURED FILTERING KIT

(75) Inventors: Jianjian Cai, Dover, MA (US); Xiaogao Liu, Dover, MA (US)

(73) Assignee: Chemrus Inc., Dover, MA (US)

( * ) Notice: Subject to any disclaimer, the term of this patent is extended or adjusted under 35 U.S.C. 154(b) by 776 days.

(21) Appl. No.: 12/461,474

(22) Filed: Aug. 12, 2009

(65) Prior Publication Data

US 2010/0038303 A1   Feb. 18, 2010

Related U.S. Application Data

(60) Provisional application No. 61/136,141, filed on Aug. 14, 2008.

(51) Int. Cl.
| | |
|---|---|
| *B01D 29/085* | (2006.01) |
| *B01L 3/00* | (2006.01) |
| *B01D 29/01* | (2006.01) |
| *G01N 1/40* | (2006.01) |

(52) U.S. Cl.
CPC .............. *B01L 3/56* (2013.01); *B01D 29/085* (2013.01); *B01D 29/01* (2013.01); *B01D 2201/204* (2013.01); *B01L 2300/0681* (2013.01); *G01N 2001/4088* (2013.01)
USPC ........................................................ 210/406

(58) Field of Classification Search
CPC ..................................................... B01D 29/085
USPC ............................................ 210/232, 406, 446
See application file for complete search history.

(56) References Cited

U.S. PATENT DOCUMENTS

| | | | | |
|---|---|---|---|---|
| 65,515 | A | * 6/1867 | Spencer | 210/406 |
| 2,449,238 | A | * 9/1948 | Lightfoot, Jr. | 210/232 |
| 3,295,686 | A | 1/1967 | Krueger | |
| 3,437,211 | A | * 4/1969 | Lindsey | 210/406 |
| 3,463,322 | A | 8/1969 | Gerarde | |
| 3,788,483 | A | 1/1974 | Conway | |
| 3,838,978 | A | * 10/1974 | Eddleman et al. | 422/535 |
| 4,251,366 | A | 2/1981 | Simon et al. | |
| 4,301,010 | A | * 11/1981 | Eddleman et al. | 210/406 |
| 4,523,934 | A | * 6/1985 | Joshua | 96/193 |

(Continued)

FOREIGN PATENT DOCUMENTS

| | | |
|---|---|---|
| EP | 321064 A1 * | 6/1989 |
| EP | 0 815 915 A1 | 7/1998 |

(Continued)

*Primary Examiner* — Thomas M Lithgow
(74) *Attorney, Agent, or Firm* — Steptoe & Johnson LLP

(57) ABSTRACT

The disposable polymer-structured filtering kit includes a disposable, polymer-structured filtering funnel with a stem having a distal tip. A flow discharge end is formed at the distal tip. Preferably, a polymer fritted filter disc is positioned in the funnel, providing filtering for liquids passing therethrough. The kit preferably also includes a glass vacuum take-off adapter having a port for connecting to a vacuum source for providing negative pressure. The adapter securely and snugly receives the funnel and maintains position of the distal tip thereof with the flow discharge end below the port, thus preventing contaminants from entering the adapter. A reusable, glass round bottle flask or a disposable vial receives the adapter and the stem of the funnel. The funnel and fritted disc are formed from disposable materials, thus removing the necessity of cleaning them following use. The adapter is reusable, since no contaminants come in contact therewith during filtering.

12 Claims, 11 Drawing Sheets

(56) References Cited

U.S. PATENT DOCUMENTS

| | | | |
|---|---|---|---|
| 4,678,576 A * | 7/1987 | Leoncavallo | 210/321.87 |
| 5,308,483 A * | 5/1994 | Sklar et al. | 210/232 |
| 5,695,639 A * | 12/1997 | Johnson | 210/474 |
| 5,948,246 A | 9/1999 | Zuk, Jr. | |
| 6,443,314 B2 * | 9/2002 | Shiraiwa et al. | 210/474 |
| 6,623,631 B1 | 9/2003 | Graus et al. | |
| 6,770,203 B2 * | 8/2004 | Leoncavallo et al. | 210/650 |
| 6,776,294 B2 * | 8/2004 | Lemonnier | 210/406 |
| 7,798,333 B2 * | 9/2010 | Zuk, Jr. | 210/406 |
| 2007/0144959 A1 | 6/2007 | Zuk, Jr. | |

FOREIGN PATENT DOCUMENTS

| | | |
|---|---|---|
| WO | WO 95/04585 A1 | 2/1995 |
| WO | WO 2007/028157 A1 * | 3/2007 |

* cited by examiner

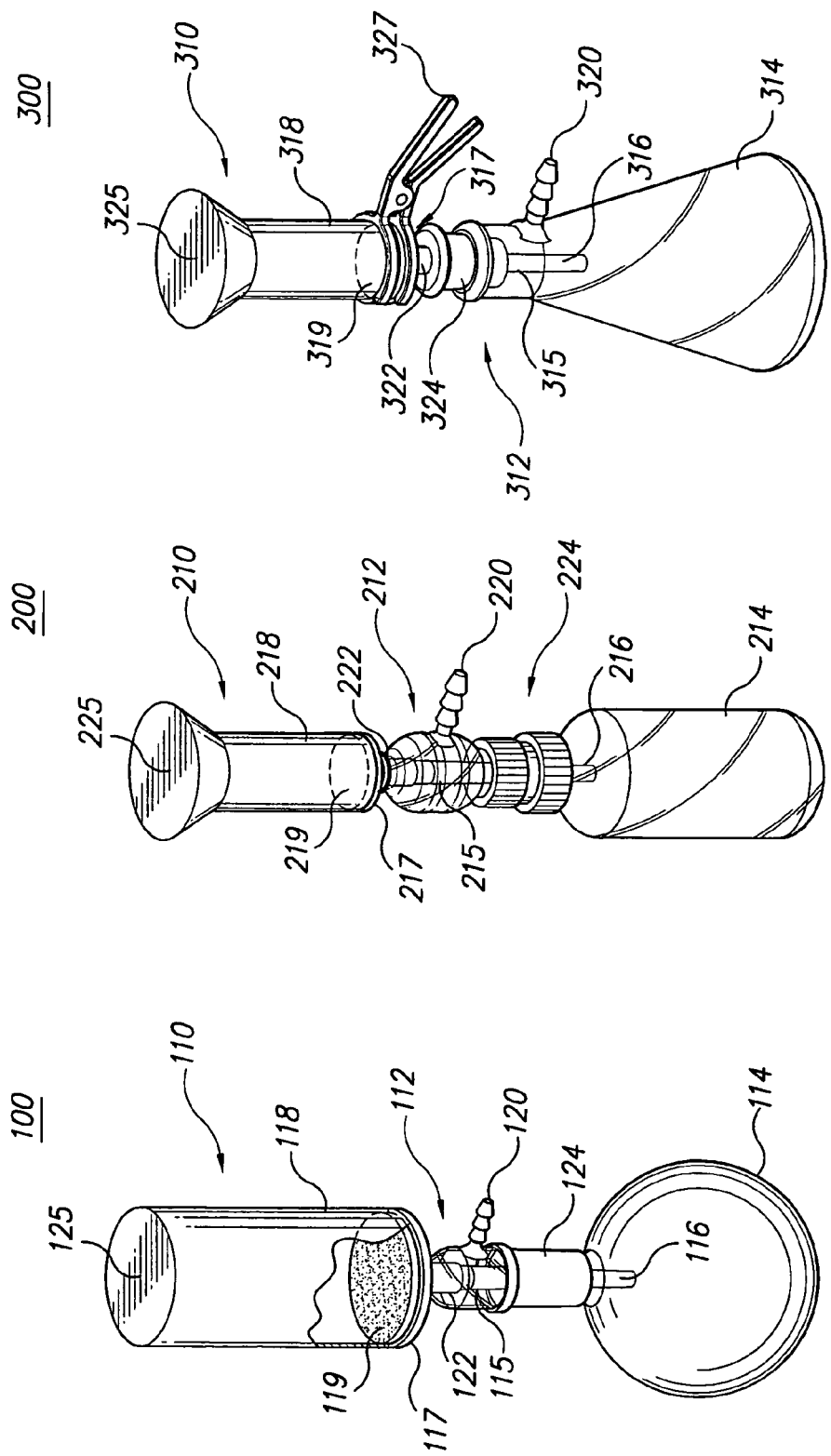

DISPOSABLE POLYMER-STRUCTURED FILTERING KIT

CROSS-REFERENCE TO RELATED APPLICATION

This application claims the benefit of U.S. Provisional Patent Application Ser. No. 61/136,141, filed Aug. 14, 2008.

BACKGROUND OF THE INVENTION

1. Field of the Invention

The present invention relates to laboratory glassware, and particularly to a disposable polymer-structured filtering kit for use in small-scale vacuum filtration of solid-liquid samples.

2. Description of the Related Art

Vacuum filtration, a common technique used in chemistry laboratories, involves passing a liquid containing a solid through a porous interface so that the solid can be trapped as the liquid flows therethrough. Typically, a vacuum filtration kit for small-scale filtration includes a filter funnel, an adapter and a receiving receptacle.

A typical vacuum filtration kit using the above three components has a vacuum port formed through the filter funnel. Such a kit typically includes a glass filter funnel with a vacuum take-off port connected to a vacuum source and a glass filtrate receptacle for receiving the solution. The funnel typically has a ground joint for coupling with a filtrate receptacle, and has a fritted glass filter disc for filtering any insoluble materials.

Another typical vacuum filtration kit may have a vacuum take-off port integrated into the adapter. The kit includes a glass filtering funnel without a ground joint, the glass adapter with the vacuum take-off port, a rubber adapter for coupling with the funnel, and a receptacle for receiving filtrate.

In yet another typical vacuum filtration kit, a vacuum take-off port is integrated into a filtrate receptacle. The kit includes a filtering funnel, the filtrate receptacle with the vacuum take-off port, and a rubber adapter for coupling the funnel with the filtrate receptacle.

With each of these vacuum filtration kits, during the filtration process, the fluid to be filtered is placed into the funnel and the filtrate receptacle is attached. Negative pressure from the vacuum is applied to the vacuum take-off port. The pressure differential caused by the vacuum causes the fluid to pass through the filter and into the receptacle. Thus, the insoluble material is collected on the fritted disc.

Following usage, all of the components of the vacuum filtration kit must be cleaned in order to eliminate contamination. However, the glassware is susceptible to accidental breakage and shattering during the cleaning process, particularly since some of the components are difficult to clean by hand. Some of the above components are relatively expensive to replace, particularly the glass filter funnel with the glass fritted disc filter, because these are typically made by hand. Additionally, the cleaning process is quite time consuming, particularly when viewed in the laboratory setting, where time is an important factor in many experiments. Thus, a disposable polymer-structured filtering kit solving the aforementioned problems is desired.

SUMMARY OF THE INVENTION

In a first embodiment, the disposable polymer-structured filtering kit includes a disposable, polymer-structured filtering funnel with a stem having a distal tip. A flow discharge end is formed at the distal tip. Preferably, a polymer fritted filter disc is positioned in the funnel, providing filtering for liquids passing therethrough. The kit preferably also includes a glass vacuum take-off adapter having a port for connecting to a vacuum source for providing negative pressure. The adapter securely and snuggly receives the funnel and maintains position of the distal tip thereof with the flow discharge end below the port, thus preventing contaminants from entering the adapter. A reusable, glass round bottle flask receives the adapter and the stem of the funnel. The funnel and fritted disc are formed from disposable materials, thus removing the necessity of cleaning them following use. The adapter does not need to be cleaned and can be reused, since no contaminants come in contact therewith during filtering. The kit is well adapted for collecting either filtrate or insoluble material.

In an alternative embodiment, the disposable, polymer-structured filtering kit includes a disposable, polymer-structured filtering funnel with a stem having a distal tip. A flow discharge end is formed at the distal tip. The funnel also preferably has a relatively wide top opening for easily receiving a liquid sample. A polymer fritted filter disc is also positioned in the funnel to provide filtering. The kit further includes a screw-threaded joint adapter having a port for connection to a vacuum source to provide negative pressure. The adapter securely and snuggly receives the funnel and maintains position of the distal tip thereof with the flow discharge end below the port, thus preventing contaminants from entering the adapter.

A disposable glass screw-threaded receiving vial is coupled to the adapter by the screw-threaded joint. The vial further receives the stem of the funnel, with the flow discharge end thereof being positioned in the vial. The funnel and fritted disc are formed from disposable materials, thus removing the necessity of cleaning them following use. The vial may also be unscrewed from the adapter for disposal. The adapter does not need to be cleaned and can be reused, since no contaminants come in contact therewith during filtering.

In a further alternative embodiment, the disposable polymer-structured filtering kit includes a disposable polymer-structured filtering funnel. The funnel has a detachable stem with a distal tip, a relatively wide top opening for easily receiving a liquid sample, and a flow discharge end positioned at the distal tip. The kit further includes a polymer adapter for securely and snuggly receiving the funnel and positioning the distal end thereof (with the flow discharge end) below the adapter. A polymer fritted filter disc is positioned between the funnel barrel and funnel base to provide filtering. An Erlenmeyer filtering flask having a vacuum port receives the adapter and the stem of the funnel, with the flow discharge end being positioned in the flask beyond the port. As above, the funnel and fritted disc are formed from disposable materials, thus removing the necessity of cleaning them following use. Further, the adapter does not need to be cleaned and can be reused, since no contaminants come in contact therewith during filtering. As a further alternative, a kit may be provided including a disposable polymer-structured filtering funnel, a glass vacuum take-off adapter, and reusable glass flask or disposable vial, as described above. The funnel, adapter and flask or vial may have any of the above-described configurations, but with the flask or vial being positioned within the adapter, rather than beneath it, as in the previous embodiments.

These and other features of the present invention will become readily apparent upon further review of the following specification and drawings.

BRIEF DESCRIPTION OF THE DRAWINGS

FIG. 1 is a perspective view of a disposable polymer-structured filtering kit according to the present invention.

FIG. 2 is a perspective view of an alternative embodiment of the disposable polymer-structured filtering kit according to the present invention.

FIG. 3 is a perspective view of another alternative embodiment of the disposable polymer-structured filtering kit according to the present.

Similar reference characters denote corresponding features consistently throughout the attached drawings.

DETAILED DESCRIPTION OF THE PREFERRED EMBODIMENTS

Figure 6:
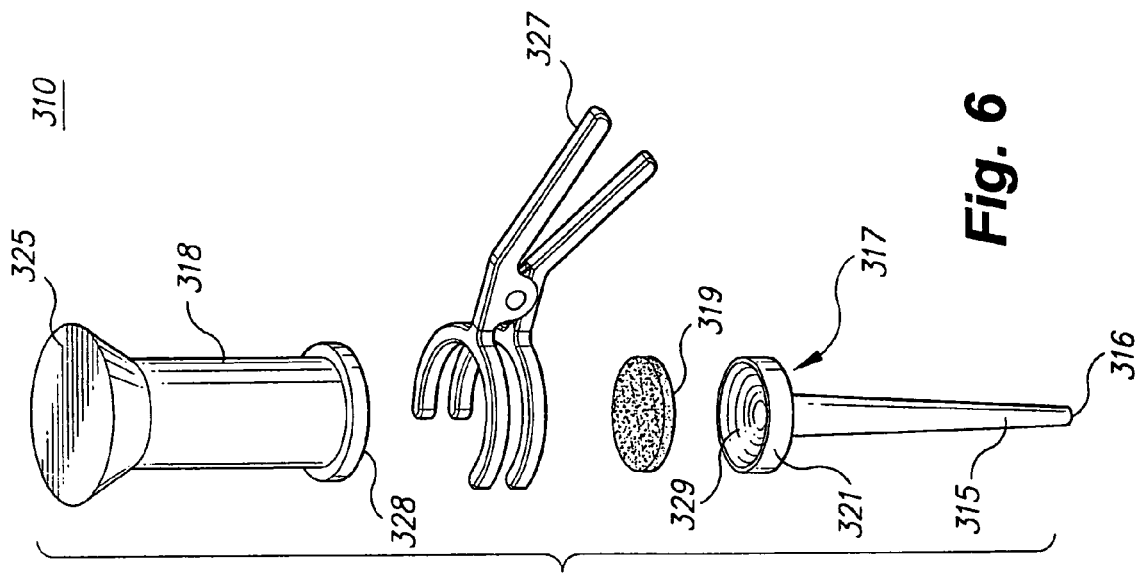
FIG. 6 is a partially exploded, perspective view of a disposable polymer-structured filter funnel of the disposable polymer-structured filtering kit of FIG. 3.

The present invention relates to disposable polymer-structured filtering kits. The kits, as will be described in detail below, each include disposable polymer-structured filter funnels, non-disposable adapters, and glass receptacles.

With reference to FIG. 1, a first embodiment of the disposable polymer-structured filtering kit, generally indicated by numeral 100, is shown. The kit 100 includes a disposable polymer-structured filtering funnel 110, a glass vacuum take-off adapter 112, and reusable glass round bottle flask 114.

The funnel 110 has a stem 115 which, as shown, is relatively long and has a flow discharge end 116 formed at the distal tip thereof. The stem 115 is relatively long such that the flow discharge end 116 extends past the glass vacuum take-off adapter 112 and into the reusable glass round bottle flask 114, as shown. The flow discharge end 116 extends into the flask 114 so as to prevent contamination of adapter 112 by filtrate when under negative pressure from an attached vacuum source (not shown). The polymer fritted filter 119 is placed on the bottom of the barrel 118 of funnel 110 for trapping insoluble materials. The funnel 110 further includes an inner joint 117 positioned between the stem 115 and barrel 118. The inner joint 117 provides a snug and secure fit between the funnel 110 and the adapter 112.

The glass vacuum take-off adapter 112 has a vacuum take-off port 120 for connection to the vacuum source, a funnel ground joint 122, and a bottom flask ground joint 124. The funnel ground joint 122 receives the stem 115 of the funnel 110 and the inner joint 117 of the funnel 110 fits the funnel ground joint 122. The stem 115 passes through the bottom flask ground joint 124 and is positioned such that the flow discharge end 116 is received within the flask 114, as shown. The flask 114 is a commonly used receptacle in chemistry laboratories, and it should be understood that the contouring and relative dimensions of flask 114 are shown for exemplary purposes only.

After filtration is complete, the funnel 110 is removed, safely discarded and disposed of, and replaced with another disposable polymer-structured filtering funnel. The adapter 112 does not need to be replaced, as the length of the stem 115 of the funnel 110 positions the distal end of the flow discharge end 116 within the flask 114, past the vacuum take-off port 120, thus removing the risk of contamination during filtration. The flask 114 is cleaned and may be reused.

FIG. 2 illustrates an alternative embodiment of the disposable polymer-structured filtering kit, generally indicated by numeral 200. The kit 200 includes a disposable polymer-structured filtering funnel 210, a screw-threaded joint adapter 212, and a removable and disposable glass screw-threaded receiving vial 214.

Funnel 210 has a stem 215 that is relatively long, as shown, with a flow discharge end 216 formed at the distal tip thereof. As in the previous embodiment, the stem 215 is long so that the flow discharge end 216 extends past the screw-threaded joint adapter 212 and into the disposable glass screw-threaded receiving vial 214. The flow discharge end 216 extends into the vial 214 such that the adapter 212 is not contaminated by filtrate when under negative pressure generated by the vacuum source. The polymer fritted filter disc 219 is placed on the bottom of the barrel 218 for trapping any insoluble materials. The funnel 210 further includes an inner joint 217 formed between the stem 215 and barrel 218. The inner joint 217 provides a snug and secure fit between the funnel 210 and the adapter 212. The funnel 210 also preferably has a relatively wide top opening 225, allowing for easy insertion therein of the liquid sample.

The screw-threaded joint adapter 212 includes a vacuum take-off port 220 for connecting to the vacuum source for providing negative pressure, along with a funnel ground joint 222 and a bottom vial joint 224. The bottom vial joint 224 is threaded to releasably screw on to the adapter 212 and the vial 214.

The funnel ground joint 222 receives the stem 215 of the funnel 210, and the inner joint 217 of the funnel 210 fits the funnel ground joint 222. The stem 215 passes through the bottom vial joint 224 such that the flow discharge end 216 is positioned within the vial 214. The vial 214 is preferably disposable.

Following filtration, the funnel 210 is removed, safely discarded and disposed of, and replaced with another disposable polymer-structured filtering funnel. The adapter 212 does not need to be replaced, because the length of the stem 215 of the funnel 210 positions the flow discharge end 216 thereof within vial 214, thus placing end 216 past the vacuum take-off port 220. The vial 214 may be easily removed, because it is removably screwed on to the adapter 212, and may be discarded. The kit 200 is preferred for either taking filtrate or taking insoluble materials that are collected by the fritted disc 219.

With reference to FIG. 3, a further alternative embodiment of the disposable polymer-structured filtering kit, generally indicated by numeral 300, is shown. The kit 300 includes a disposable polymer-structured filtering funnel 310, an adapter 312, and an Erlenmeyer shaped filtering flask 314 with a vacuum port 320.

A funnel base 321 (best seen in FIG. 6) has a stem 315 that is relatively long with a flow discharge end 316 formed at the distal tip. As in the previous embodiments, the stem 315 is long so that the flow discharge end 316 extends past the adapter 312, into the Erlenmeyer shaped filtering flask 314, and past the vacuum port 320 of the flask 314. The flow discharge end 316 extends past the vacuum port 320 such that the filtrate does not contaminate the adapter 312 during vacuum filtration. The funnel base 321 further includes an inner joint 317 at the top of the stem 315. The inner joint 317 provides a snug fit with the adapter 312. The funnel 310 also preferably has a relatively wide top opening 325, for easy reception of the liquid sample. Additionally, a clamp 327 is preferably provided for holding the funnel barrel 318 to the funnel base 321, with the polymer fritted filter disc 319 being positioned therebetween.

The adapter 312 has a glass funnel ground joint 322 and a polymer stopper joint 324. The glass funnel ground joint 322 receives the stem 315 of the funnel 310, and the inner joint 317 of the funnel 310 fits the funnel ground joint 322. The stem 315 then passes through the polymer stopper joint 324 and is positioned such that the flow discharge end 316 is located below the vacuum port 320 of the flask 314.

After filtration is complete, the funnel 310 is removed, safely discarded and disposed of, and replaced with another disposable polymer-structured filtering funnel. The adapter 312 does not need to be replaced, because the length of the stem 315 of the funnel 310 and the positioning of the distal end of the flow discharge end 316 within flask 314 is positioned beyond the vacuum take-off port 320 of the flask 314, thus preventing contamination of adapter 312. Fritted disc 319 can similarly be disposed of. The kit 300 is preferred for taking insoluble materials that are collected by the fritted disc 319, since the funnel 310 can be disassembled so that the solid materials are easily removed.

Figure 4:
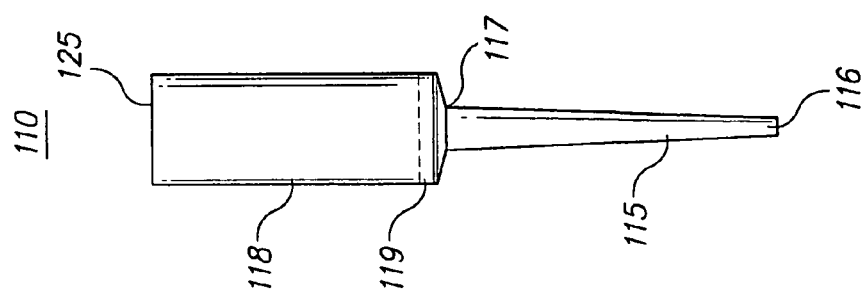
FIG. 4 is a side view of a disposable polymer-structured filter funnel of the disposable polymer-structured filtering kit of FIG. 1.

FIG. 4 better illustrates the disposable polymer-structured filter funnel 110 of FIG. 1. The disposable filter funnel 110 is preferably barrel-shaped, having an open upper end 125 and a lower stem 115 having a flow discharge end 116. Funnel 110, formed from a low cost polymer material, and fritted filter disc 119 are both disposable and may be easily replaced.

The filtering funnel 110 and fritted filter disc 119 must resist corrosion from various organic solvents. Accordingly, an inexpensive polypropylene is preferably selected as the material of funnel 110. However, other polymer materials may also be utilized, such as acrylic, polycarbonate, styrene, polyfluoroethylene, polyvinylidene fluoride, or polyethylene. The minimum length of the stem 115, to position the flow discharge end 116 within flask 114, is preferably approximately twenty mm. The preferred length for the stem 115 is approximately eighty mm. The top end of the stem 115 includes inner joint 117, which fits the funnel ground joint 122 of the glass adapter 112 tightly to prevent leaking. The size of inner joint 117 is preferably between approximately five and sixteen mm in diameter, and between approximately five and twenty mm in length. It should be understood that the funnel 110 may be used in combination with the filtering kits of FIGS. 2 and 3. An exemplary internal volume for 110 is approximately 40 mL.

Figure 5:
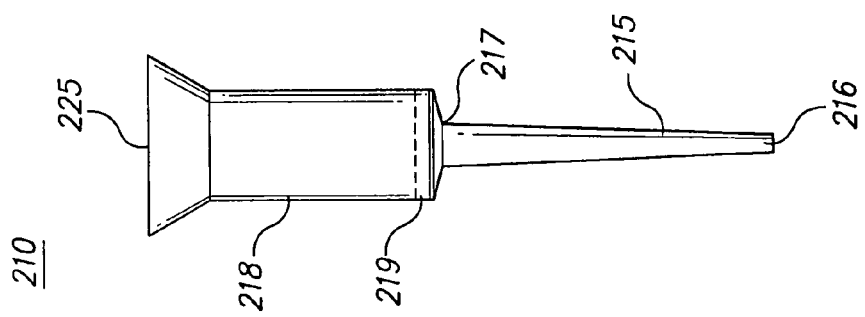
FIG. 5 is a side view of a disposable polymer-structured filter funnel of the disposable polymer-structured filtering kit of FIG. 2.

FIG. 5 illustrates the disposable polymer-structured filter funnel 210 of FIG. 2. Funnel 210 preferably has a relatively wide top opening 225, as shown, and has contouring and dimensions similar to those described above with regard to funnel 110. However, barrel 218 has an open upper end 225. The top end of the stem 215 has an inner joint 217, which fits the funnel ground joint 222 of the glass adapter 212 tightly to prevent leaking. The size of inner joint 217 is preferably between five and sixteen mm in diameter, and from between five and twenty mm in length. It should be understood that the funnel 210 may be used in combination with the filtering kits of FIGS. 1 and 3. As noted above, funnel 210 is designed for relatively small quantities of fluid. The exemplary internal volume for funnel 110 is given above as being approximately 40 mL. A corresponding exemplary internal volume for funnel 210 is 18 mL. It should be understood that the funnels may have any desired dimensions, or be provided in sets of varying sizes, dependent upon the particular needs of the user.

FIG. 6 illustrates the disposable polymer-structured filter funnel 310 for trapping solid samples of FIG. 3. The barrel 318 has an open top end 325 and an open bottom end 328. The barrel 318 uses a wider open end 325 (similar to that described above with regard to upper end 225 of funnel 210) for transferring relatively small volumes of fluid samples. The open bottom end 328 is provided for easily removing solid samples from the funnel 310.

A concavity 329 is formed at the top end of the funnel base 321, as shown. The filter disc 319 is placed in the concavity 329, enclosing the filter disc 319 when the kit is assembled.

The metal clamp 327 is used to tightly clamp bottom end 328 of the barrel 318 and the top end of the base 321. As shown, the barrel 318 forms an upper portion of the funnel, with the stem 317 forming a detachable lower portion. This arrangement is adapted for trapping solid samples and transferring relatively small volumes of liquid samples. It should be understood that the funnel 310 may be used in combination with the filtering kits of FIGS. 1 and 2. Preferably, filter discs 119, 219 and 319 are formed from a polymer material, such as polyethylene, for example, having a relatively coarse or medium porosity. Alternatively, a conventional glass fritted filter disc may also be utilized.

Figure 7:
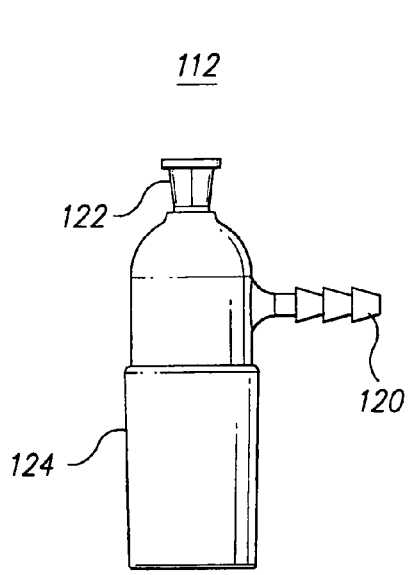
FIG. 7 is a side view of a vacuum take-off adapter of the disposable polymer-structured filtering kit of FIG. 1.
Figure 14:
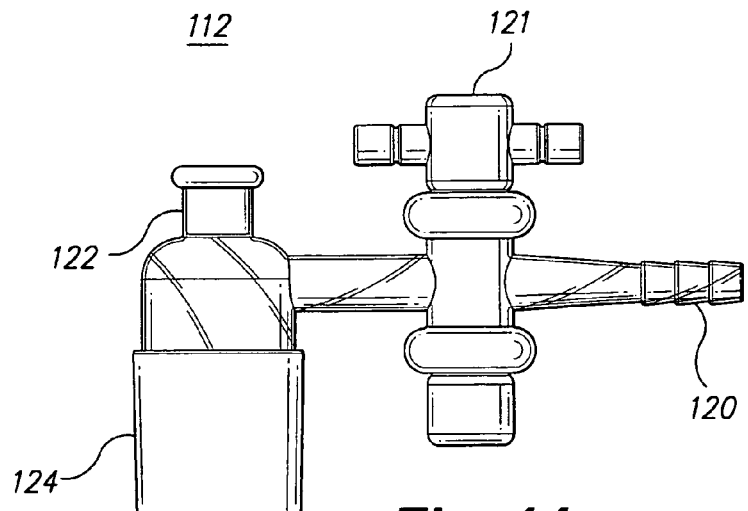
FIG. 14 is a side view of an alternative embodiment of a vacuum take-off adapter of the disposable polymer-structured filtering kit of FIG. 1 having a straight vacuum arm and a stopcock disposed in the arm.

FIG. 7 illustrates the vacuum take-off adapter 112, with a bottom flask ground joint 124 and the funnel ground joint 122, of FIG. 1. The vacuum take-off port 120 is formed on the side of adapter 112 for connection to the vacuum source. The funnel ground joint 122 on the top end is coupled with inner joint 117 of the funnel 110, and is preferably between approximately five and sixteen mm in diameter, and between five and twenty mm in length. The bottom flask ground joint 124 coupled with the receiving receptacle or flask 114 preferably is manufactured in sizes of 14/20, 19/22, 24/25, 24/40 or 29/42. As is conventionally known, a size of 14/20, for example, means that the bottom flask ground joint 124 is fourteen mm in diameter, and twenty mm in length. The bottom ground joint 124 fits reusable glass round bottle flasks, such as exemplary flask 114 of FIG. 1. Adapter 112 is preferably formed from conventional glass, though, alternatively, may be formed from a polymer material, metal or any other suitable material. FIG. 14 illustrates an alternative embodiment of adapter 112 in which stopcock or valve 121 may be integrated into the vacuum take-off port 120 in order to adjust the vacuum and prevent the filtrate from being sucked into the vacuum line.

Figure 8:
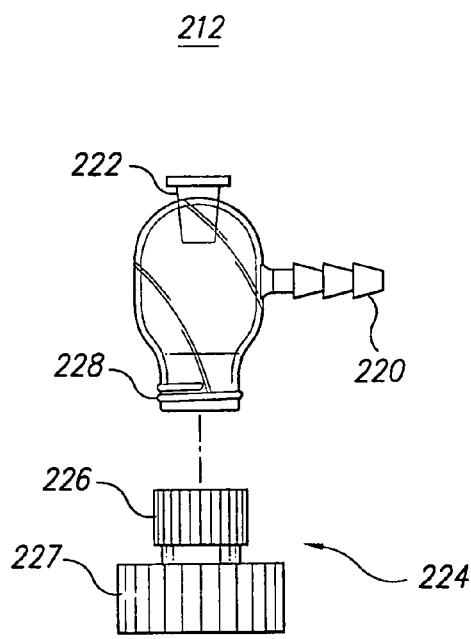
FIG. 8 is a partially exploded view of a vacuum take-off adapter of the disposable polymer-structured filtering kit of FIG. 2.
Figure 15:
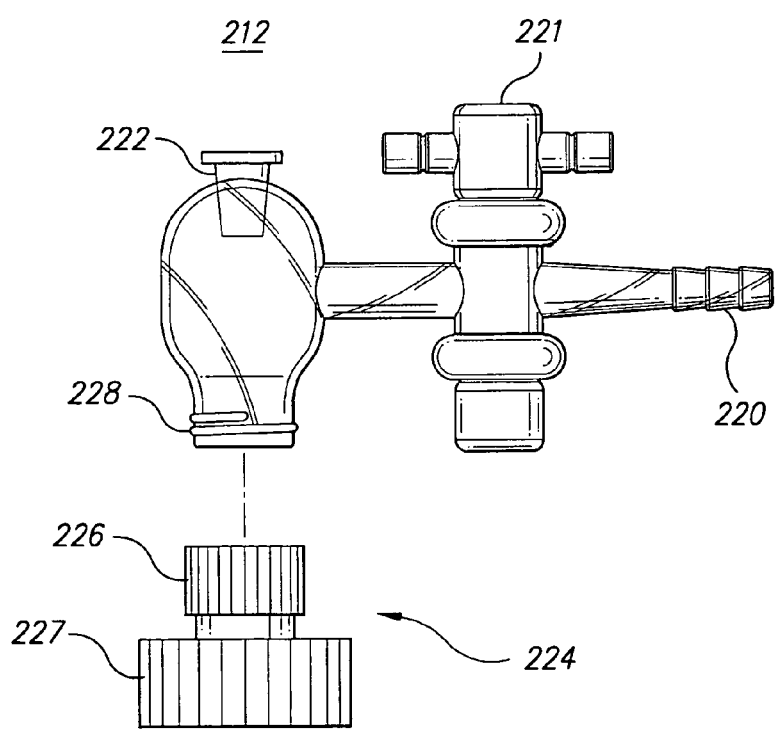
FIG. 15 is a partially exploded view of another alternative embodiment of a vacuum take-off adapter of the disposable polymer-structured filtering kit of FIG. 2 having a straight vacuum arm and a stopcock disposed in the arm.

FIG. 8 illustrates the vacuum take-off adapter 212, with a bottom vial joint 224 and the funnel ground joint 222, of FIG. 2. The vacuum take-off glass adapter 212, which is designed for coupling with disposable glass vial 214, is shown joined to vial 214 in FIG. 2. The adapter 212 includes funnel ground joint 222 on its top end, a bottom vial joint 224 on its bottom end, and a vacuum take-off port 220 projecting from its side. The funnel ground joint 222 fits the inner joint 217 of the funnel 210, and is preferably between five and sixteen mm in diameter, and between five and twenty mm in length. The bottom vial joint 224 has a top threaded joint 226 for screwing to the glass adapter 212, having threads 228, and a bottom threaded joint 227 for screwing to the disposable glass vial 214, as shown in FIG. 2. The thread of the joint 226 preferably uses G.P.I. (Glass Packaging Institute) 20-400 thread. The inside diameter of the threaded joint 226 is approximately twenty mm. The numeral "400" designates a specific style of the finish. FIG. 15 illustrates an alternative embodiment of adapter 212. As shown, a stopcock or valve 221 may be integrated into the vacuum take-off port 220 in order to adjust the vacuum and prevent the filtrate from being sucked into the vacuum line. Adapter 212 is preferably formed from conventional glass, but may alternatively be formed from polymer materials, metal or any other suitable material.

Figure 9:
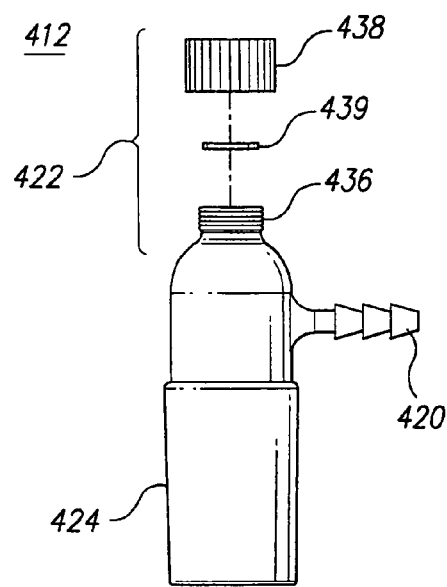
FIG. 9 is a partially exploded view of an alternative vacuum take-off adapter of the disposable polymer-structured filtering kit of FIG. 1.

FIG. 9 illustrates an alternative vacuum take-off adapter 412, for use with the kit of FIG. 1, with a bottom ground joint 424 and a filter funnel screw-threaded joint 422. The glass adapter 412 can replace adapter 112. The adapter 412 has an interface screw-threaded joint 436 on its top end, with an inner diameter between approximately five and sixteen mm. A cap 438, having an aperture formed therethrough, and a sealing ring 439 are placed on the interface screw-threaded joint 436 to seal an attached filter funnel, which functions to adjust a position of a flow discharge end of the funnel. A vacuum take-off port 420 is further provided.

Figure 10:
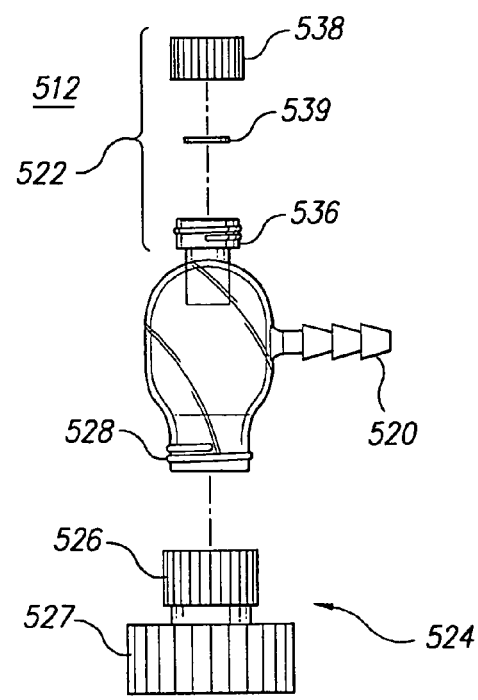
FIG. 10 is a partially exploded view of an alternative vacuum take-off adapter of the disposable polymer-structured filtering kit of FIG. 2.

FIG. 10 illustrates an alternative vacuum take-off adapter 512, for use with the kit of FIG. 2, having a bottom vial joint 524 and a funnel screw threaded joint 522. A side vacuum port 520 extends outwardly, as shown. The adapter 512 includes a funnel screw-threaded joint 536 on its top end. To connect the adapter 512 to a funnel, a cap 538, having an aperture formed therethrough, is provided for receiving a flow discharge end of the funnel, and positioning the flow discharge end beneath the side vacuum port 520. A sealing ring 539 and the cap 538 are placed on the funnel screw-threaded joint 536 to seal an attached funnel. The bottom vial joint 524 has an interface screw-threaded joint 526 that attaches to the adapter 512 by threads 528, and a vial screw-threaded joint 527 for coupling with a receiving receptacle or vial.

Figure 11:
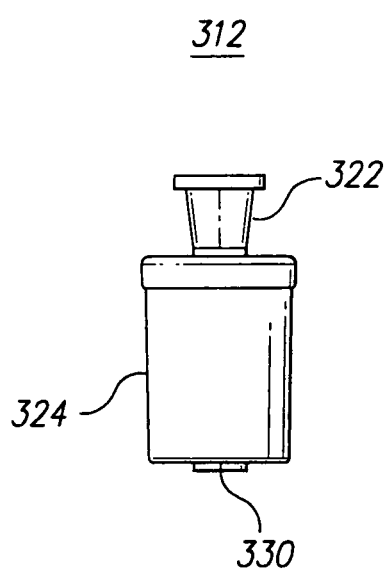
FIG. 11 is a side view of a polymer adapter of the disposable polymer-structured filtering kit of FIG. 3.

FIG. 11 illustrates adapter 312 of the kit of FIG. 3. Adapter 312 includes a stopper 324 having an aperture formed centrally therethrough. The adapter 312 is designed for coupling with a vacuum Erlenmeyer shaped filtering flask, such as exemplary flask 314 of FIG. 3. The stopper 324 is formed from a polymer material, such as rubber, silicone rubber or neoprene. Glass tubing 330, with funnel ground joint 322 formed on its top end, is inserted tightly into the center of the stopper 324. The glass funnel ground joint 322 has a diameter between approximately five and sixteen mm, and a length between approximately five and twenty mm.

Figure 12:
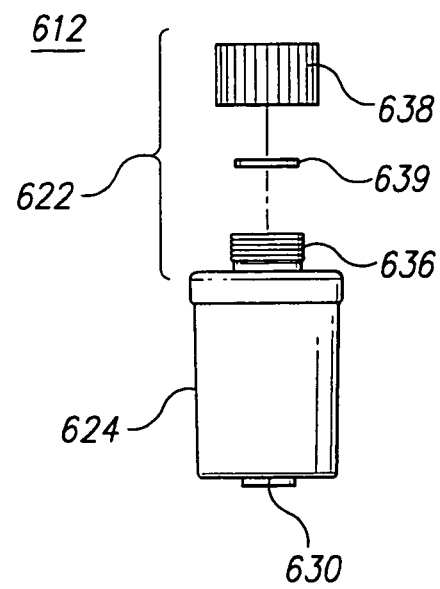
FIG. 12 is a partially exploded side view of an alternative polymer adapter of the disposable polymer-structured filtering kit of FIG. 3.

FIG. 12 illustrates an alternative adapter 612, for use with the kit of FIG. 3, with a screw-threaded joint 622 on its top end. The stopper 624 is formed from polymer materials, such as rubber, silicone rubber or neoprene and is similar to stopper 324 except for the screw-threaded joint 622. The adapter 612 is used to couple a filter funnel with the vacuum Erlenmeyer shaped filtering flask. A glass screw threaded tube 630 is inserted tightly into the center of the stopper 624. A cap 638, having an aperture formed therethrough and a sealing ring 639, are placed on a screw-threaded top 636 of the adapter 612 to seal an attached filter funnel. Thus, the flow discharge end of the funnel is positioned below the vacuum take-off port when the kit is assembled.

Figure 13:
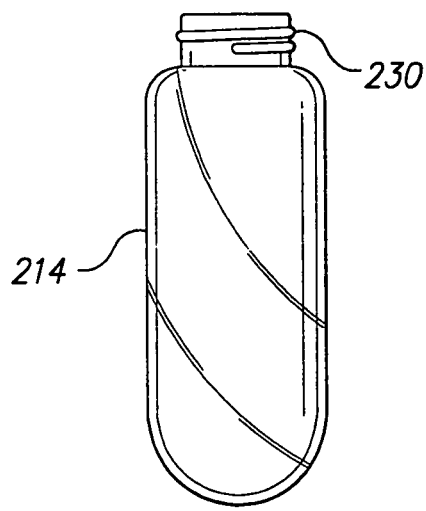
FIG. 13 is a side view of a disposable glass-receiving receptacle of the disposable polymer-structured filtering kit of FIG. 2.

FIG. 13 illustrates the disposable glass-receiving receptacle 214 of FIG. 2. Receptacle 214 includes a screw-threaded joint 230. The diameter of the threaded joint 230 is preferably between twenty and thirty mm. A typical diameter of the joint 230 is approximately twenty-three mm, fitting G.P.I. 20-400 thread. The vial 214 has a semi-round bottom to prevent cracking under negative or positive pressure. The volume of the vial 214 is preferably between 60 and 300 mL. Multiple vials having differing volumes may be provided, such as an 100 mL vial and a 200 mL, for example.

Figure 16:
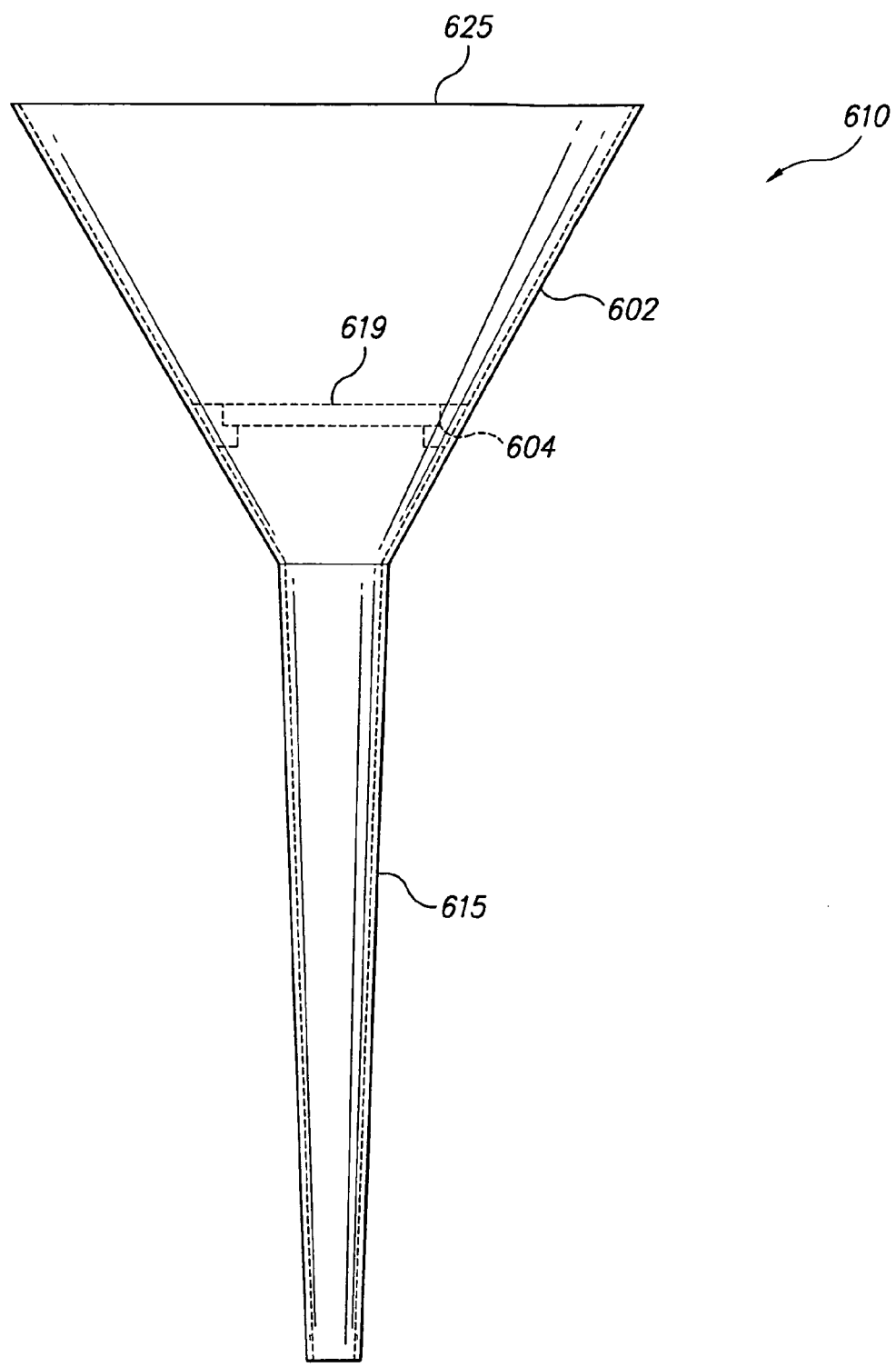
FIG. 16 is a side view of an alternative embodiment of a disposable polymer-structured filter funnel of the disposable polymer-structured filtering kit according to the present invention, the funnel being conical and having a fritted filter disk or a polymer disk supported by an annular flange in the funnel bowl.
Figure 20:
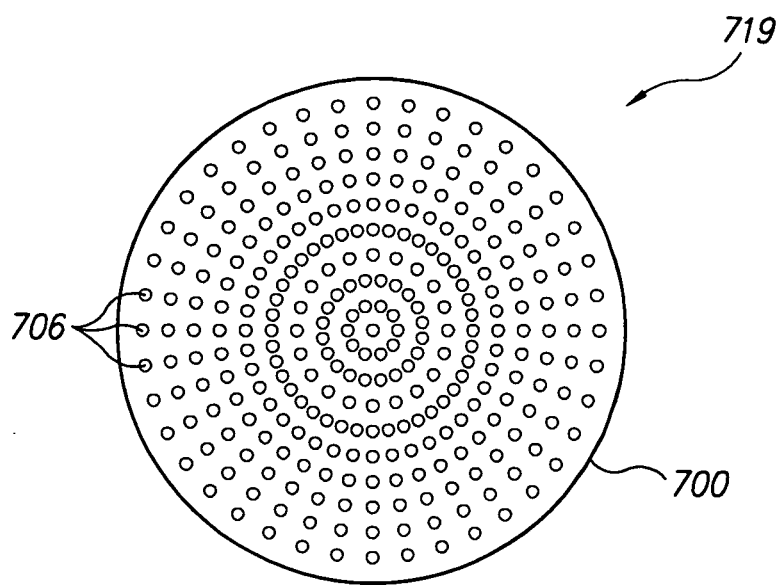
FIG. 20 is a plan view of an alternative embodiment of a filter disc of the disposable polymer-structured filtering kit according to the present invention, showing the hole pattern.
Figure 21:
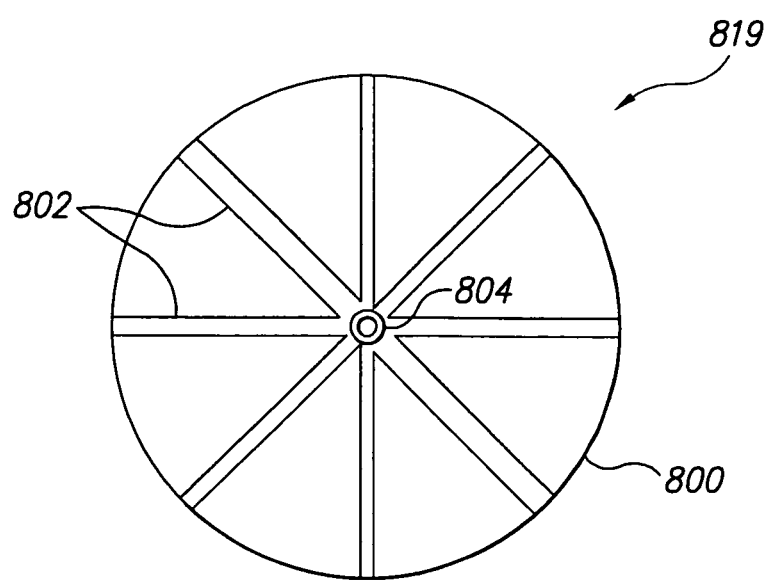
FIG. 21 is a plan view of another alternative embodiment of a filter disc of the disposable polymer-structured filtering kit according to the present invention, showing a pattern of slits or slots.

FIG. 16 illustrates an alternative cone-shaped disposable filter funnel 610, to be used with any of the kits of FIG. 1, 2 or 3. Funnel 610 includes an upper portion 602, having a substantially frusto-conical contour, with a long stem 615 projecting downwardly therefrom. The upper portion has an open upper end 625, and an annular flange 604 is formed within the upper portion 602, adjacent the junction between the lower end of upper portion 602 and the stem 615, as shown. Filter disc 619 is removably received by annular flange 604, as shown. As described above, filter disc may be formed from a disposable, porous polymeric material, or may be formed from fritted glass or the like. As a further alternative, the filter disc 619 may be formed as a polymer disc. FIG. 20 illustrates exemplary polymer disc 619, having a main body 700 with a plurality of relatively small apertures or pores 706 formed therethrough. Polymer disc 619 is covered in disposable filter paper or a porous, polymeric membrane in order to trap the solute or insoluble materials. FIG. 21 illustrates an alternative polymer disc 819 having a main body 800 and a plurality of slots 802 formed in an upper surface thereof. A central aperture or pore 804 is further formed therethrough.

Figure 17:
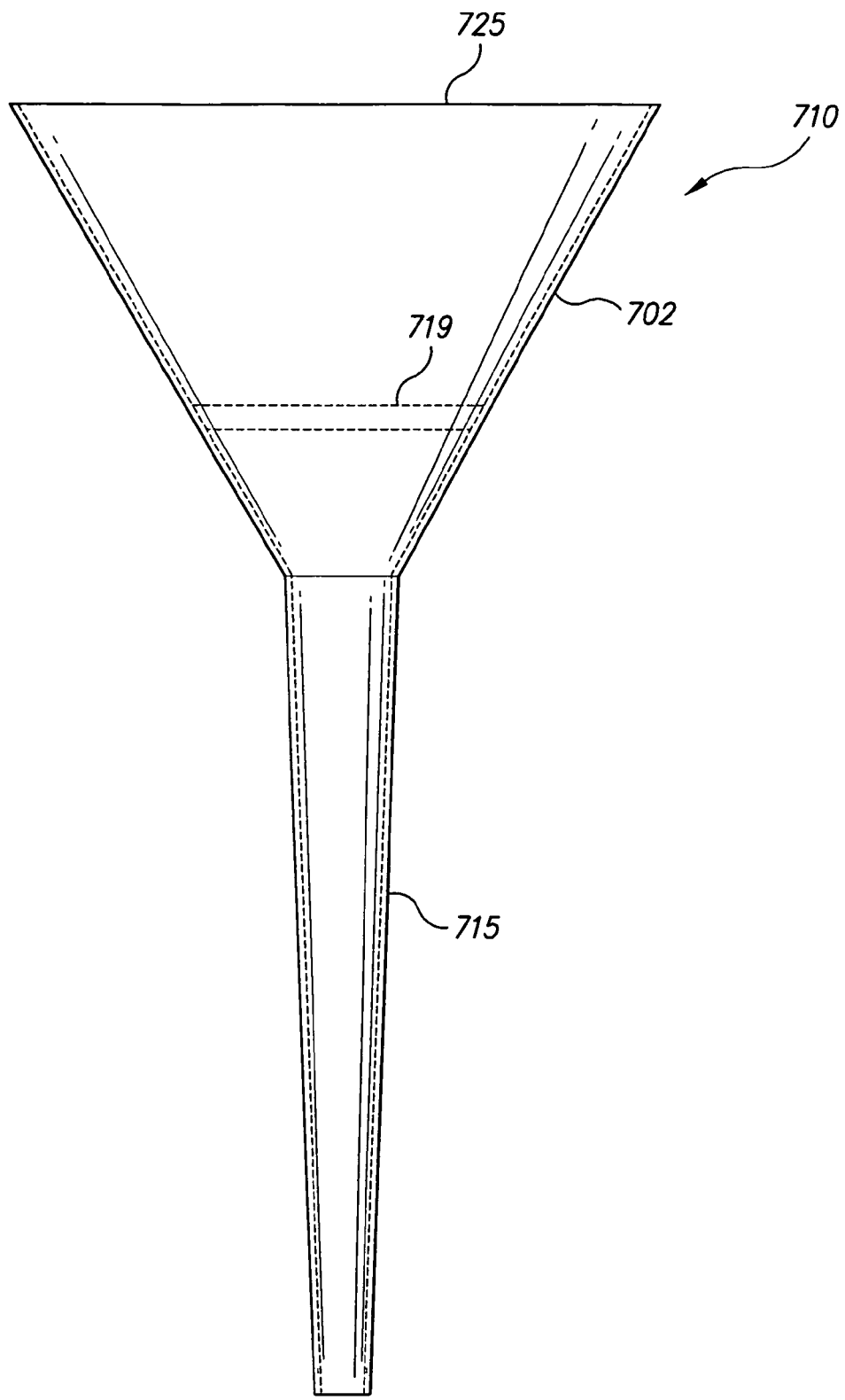
FIG. 17 is a side view of another alternative embodiment of a disposable polymer-structured filter funnel of the disposable polymer-structured filtering kit according to the present invention, the funnel being conical and having a polymer plate disposed in the funnel bowl.

FIG. 17 illustrates an alternative cone-shaped disposable filter funnel 710, similar to funnel 610 described above. Funnel 710 includes an upper portion 702, having a substantially frusto-conical contour, with a long stem 715 projecting downwardly therefrom. The upper portion 702 has an open upper end 725. Instead of the annular flange 604 of funnel 610, the filter disc 719 is formed integrally with the upper portion 702, as shown.

Figure 18:
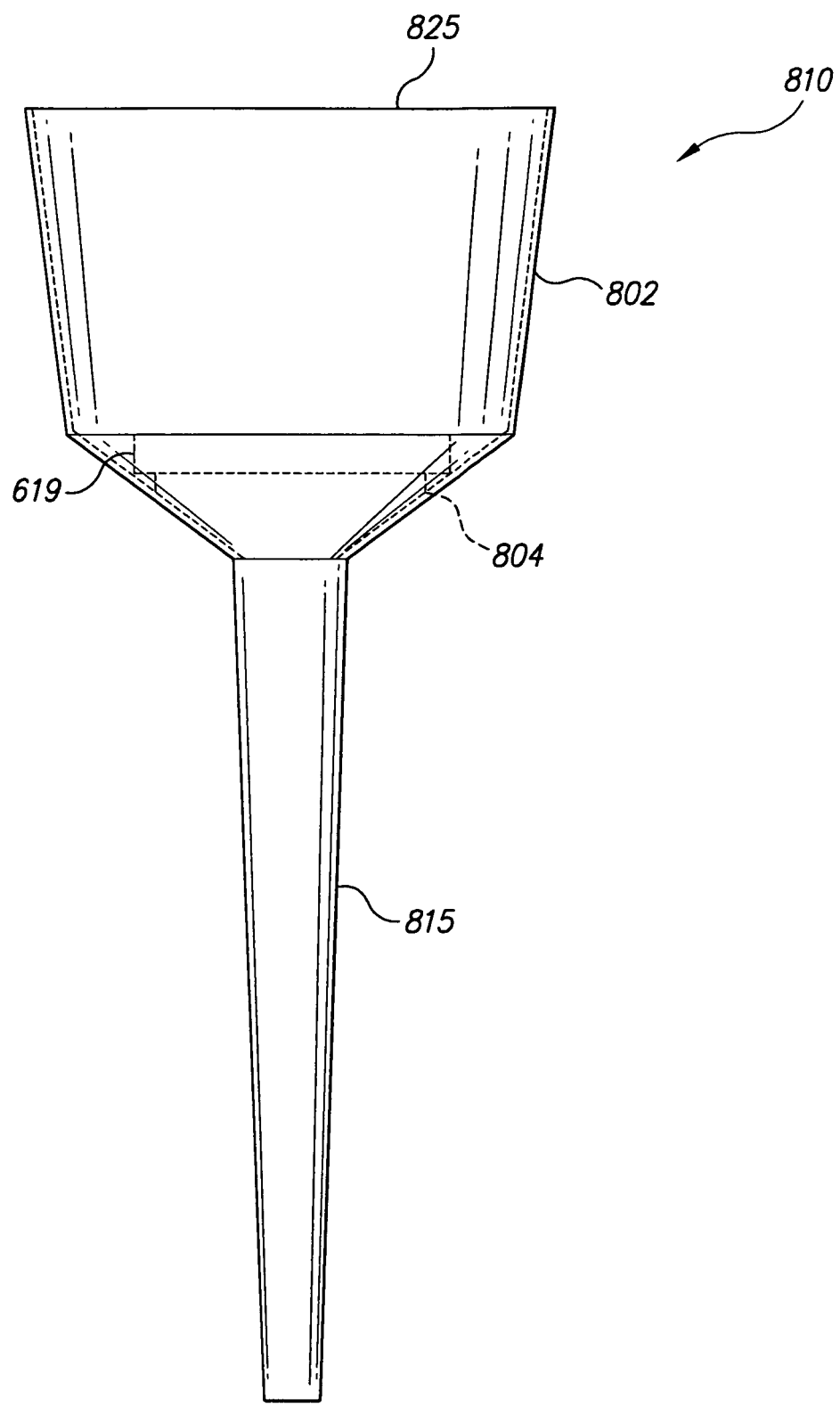
FIG. 18 is a side view of another alternative embodiment of a disposable polymer-structured filter funnel of the disposable polymer-structured filtering kit according to the present invention, the funnel being cylindrical and having a fritted filter disk or polymer disk supported by an annular flange in the funnel bowl.

FIG. 18 illustrates a further alternative filter funnel 810, to be used with any of the kits of FIG. 1, 2 or 3. Funnel 810 includes a substantially cylindrical upper portion 802 with a long stem 815 projecting downwardly therefrom. The upper portion 802 has an open upper end 825, and an annular flange 804 is formed within the upper portion 802, adjacent the junction between the lower end of upper portion 802 and the stem 815, as shown. Filter disc 619 is removably received by annular flange 804, as shown. As described above, filter disc 619 may be formed from a disposable, porous polymeric material, or may be formed from fritted glass or the like. Filter disc 619 may, alternatively, be replaced by filter discs 719 or 819, as desired. As a further alternative, the filter disc 619 is wrapped in disposable filter paper.

Figure 19:
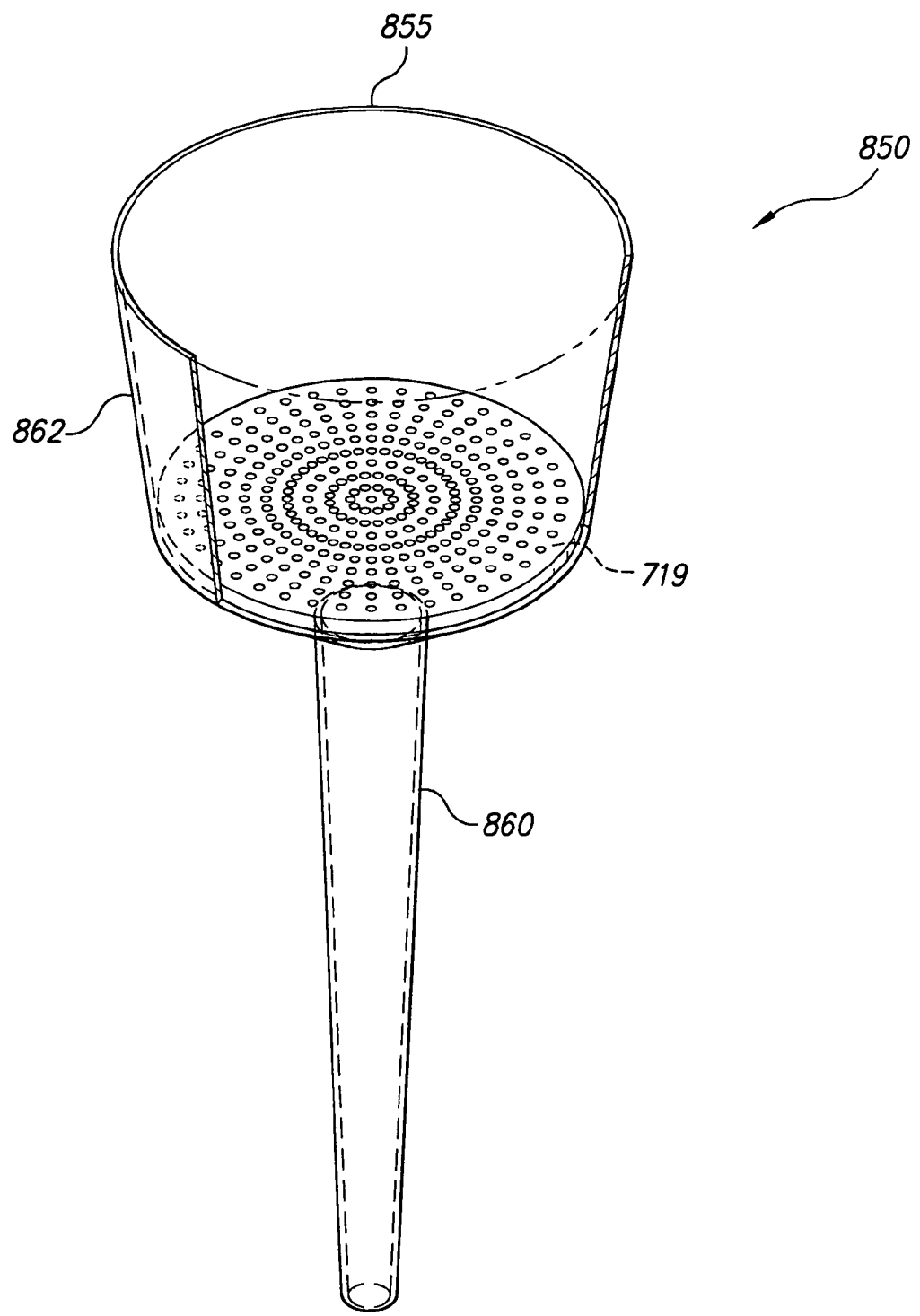
FIG. 19 is a perspective view of another alternative embodiment of a disposable polymer-structured filter funnel of the disposable polymer-structured filtering kit according to the present invention, the funnel being cylindrical and having a polymer plate disposed in the funnel bowl.

FIG. 19 shows an alternative filter funnel 850, similar in contour to filter funnel 810, described above, but lacking the inner, annular flange 804. Funnel 850 includes a lower, stem portion 860 and an upper portion 862, having an open, upper end 855. A filter disc, such as filter disc 719, described above, for example, is received within the upper portion 862 and the filter funnel 850 and/or the filter disc 719 are sized such that the filter disc 719 mates with the inner circumferential wall of the funnel 850 at or near the junction between the upper portion 862 and the lower portion 860. The filter disc 719 is held in place by frictional engagement with the inner wall. Filter disc 719 may, alternatively, be replaced by filter discs 819, as desired. As a further alternative, the filter disc 719 is wrapped in disposable filter paper.

Figure 22:
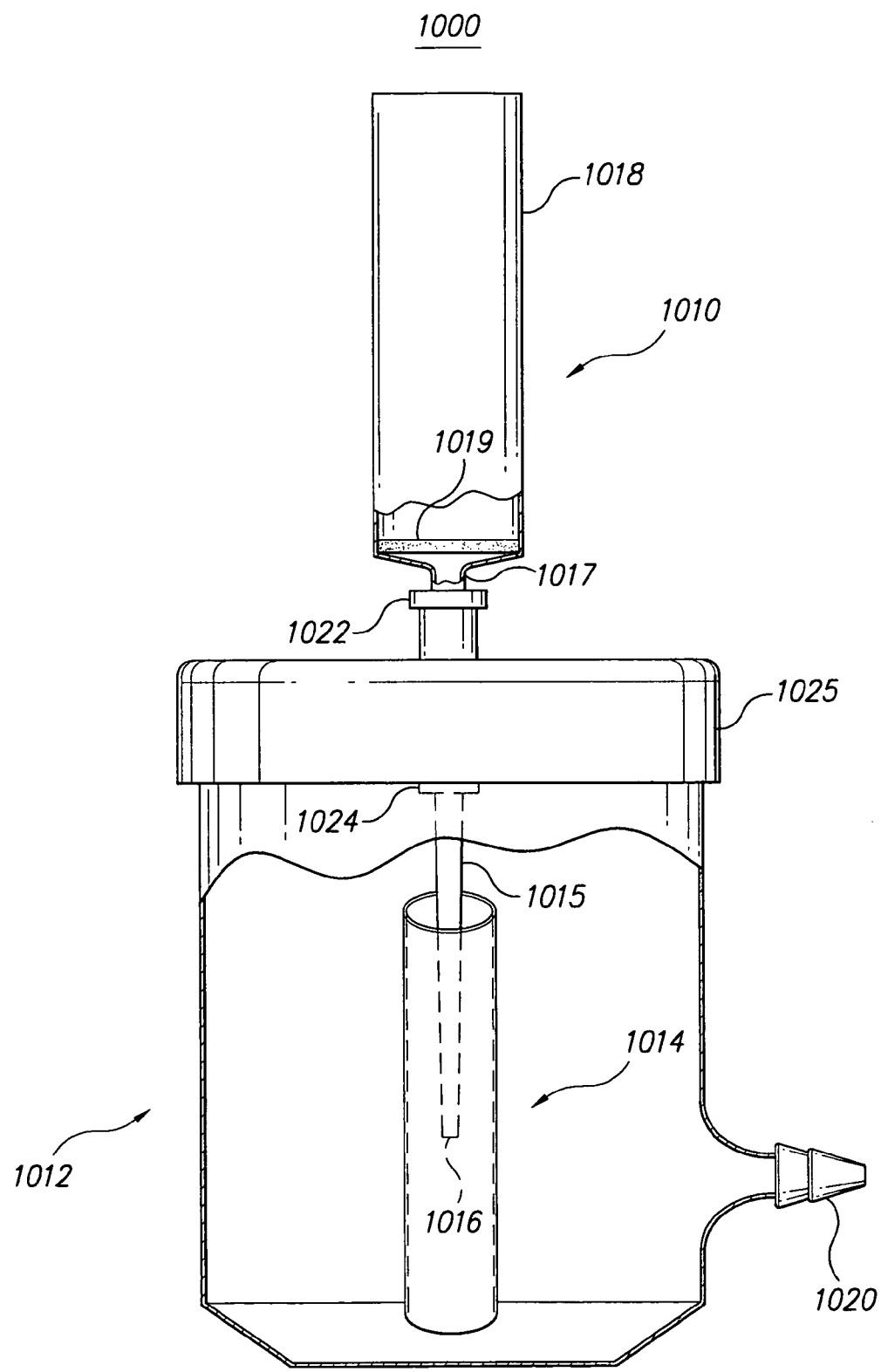
FIG. 22 is a side view of another alternative embodiment of the disposable polymer-structured filtering kit according to the present invention.

With reference to FIG. 22, another embodiment of the disposable polymer-structured filtering kit, generally indicated by numeral 1000, is shown. The kit 1000 includes a disposable polymer-structured filtering funnel 1010, a glass vacuum take-off adapter 1012, and reusable glass flask or disposable vial 1014. Funnel 1010, adapter 1012 and flask or vial 1014 may have any of the above-described configurations, as FIG. 22 is intended to illustrate an alternative where flask or vial 1014 is positioned within adapter 1012, rather than beneath it.

As in the previous embodiments, the funnel 1010 has a stem 1015 with a flow discharge end 1016 formed at the distal tip thereof. The stem 1015, however, extends within the glass vacuum take-off adapter 1012 and into the reusable flask or disposable vial 1014. The flow discharge end 1016 extends into the flask 1014 to prevent contamination of adapter 1012 by filtrate when under negative pressure from an attached vacuum source (not shown). A polymer fritted filter 1019 is placed on the bottom of the barrel 1018 of funnel 1010 for trapping insoluble materials. The funnel 1010 further includes an inner joint 1017 positioned between the stem 1015 and barrel 1018. The inner joint 1017 provides a snug and secure fit between the funnel 1010 and the adapter 1012.

The glass vacuum take-off adapter 1012 has a vacuum take-off port 1020 for connection to the vacuum source, and a funnel ground joint 1022. A cap 1025, formed from a polymer material, is further provided for sealing the adapter. The funnel ground joint 1022 receives the stem 1015 of the funnel 1010 and the inner joint 1017 of the funnel 1010 fits the funnel ground joint 1022. Rather than the bottom flask ground joint of the previous embodiments, a tube 1024 is provided within the adapter 1012, as shown, at the upper end thereof, so that stem 1015 passes through the tube 1024 and is positioned so that the flow discharge end 1016 is received within the flask or vial 1014. Glass tube 1024, with funnel ground joint 1022 on its top end, are inserted tightly through the center of cap 1025. The flask or vial 1014 is a commonly used receptacle in chemistry laboratories, and it should be understood that the shape and relative dimensions of flask 1014 are shown for exemplary purposes only. The glass funnel ground joint 1022 preferably has a diameter between approximately five and sixteen mm, and a length between approximately five and twenty mm.

After filtration is complete, the funnel 1010 is removed, safely discarded and disposed of, and replaced with another disposable polymer-structured filtering funnel. The cap 1025 of adapter 1012 is also opened to remove the flask or vial 1014. The adapter 1012 does not need to be replaced, as the length of the stem 1015 of the funnel 1010 positions the distal end of the flow discharge end 1016 within the flask or vial 1014, thus removing the risk of contamination during filtration.

It is to be understood that the present invention is not limited to the embodiments described above, but encompasses any and all embodiments within the scope of the following claims.

We claim:

1. A disposable polymer-structured filtering kit, comprising:
   a disposable filtering funnel having a first diameter, an upper portion and a lower portion, the lower portion terminating at an inner joint;
   a stem extending from the inner joint, the stem having a flow discharge end positioned at a distal tip thereof;
   a filter disc within the funnel, the disposable filtering funnel being constructed of a polymer resistant to organic solvent;
   a cleanse-free vacuum take-off adapter having a port adapted for connection to an external vacuum source, the vacuum take-off adapter having a bulbous portion, a funnel engaging end and a flask or vial engaging end, the flask or vial engaging end opposite the funnel engaging end, wherein the funnel engaging end of the vacuum take-off adapter has a second diameter that is less than the first diameter and wherein the funnel engaging end of the vacuum take-off adapter releasably receives the inner joint, and wherein a top surface of the bulbous portion contacts the funnel engaging end and a bottom surface of the bulbous portion contacts the flask or vial engaging end, and wherein the bulbous portion extends between the funnel engaging end and the flask or vial engaging end; and
   a bottle flask or vial releasably connected to the adapter at the flask or vial engaging end of the adapter, the bottle flask or vial including a neck at a top portion of the bottle flask or vial, wherein the flask or vial engaging end of the adapter is configured to be inserted into the neck;
   wherein the distal tip of the stem is positioned below the port of the vacuum take-off adapter when the funnel, adapter and flask are assembled.

2. The disposable polymer-structured filtering kit as recited in claim 1, wherein the filter disc is formed from a disposable, porous polymeric material.

3. The disposable polymer-structured filtering kit as recited in claim 1, wherein the polymeric material of the disposable filtering funnel and a porous polymeric material of the filter disc are selected from the group consisting of polypropylene, polyethylene, acrylic, polycarbonate, styrene, polyfluoroethylene, and polyvinylidene fluoride.

4. The disposable polymer-structured filtering kit as recited in claim 1, wherein the filter disc comprises a main body having at least one aperture formed therethrough.

5. The disposable polymer-structured filtering kit as recited in claim 4, further comprising at least one sheet of filter paper, the filter disc being releasably wrapped in the at least one sheet of filter paper.

6. The disposable polymer-structured filtering kit as recited in claim 1, wherein the stem is between twenty millimeters and eighty millimeters.

7. The disposable polymer-structured filtering kit as recited in claim 1, wherein the stem has an inner joint, which tightly fits the funnel engaging end of the adapter.

8. The disposable polymer-structured filtering kit as recited in claim 1, wherein the lower portion of the disposable filtering funnel is a smooth polymer surface in direct contact with a smooth surface of the funnel engaging end of the adapter.

9. The disposable polymer-structured filtering kit as recited in claim 1, wherein the flask or vial engaging end of the adapter is a standard taper outer joint in size of 14/20, 19/22, 24/25, 24/40, 29/42.

10. The disposable polymer-structured filtering kit as recited in claim 1, wherein the filter disc substantially contacts a bottom surface of the funnel.

11. The disposable polymer-structure filtering kit as recited in claim 1, wherein the port extends from the bulbous portion of the cleanse-free vacuum take-off adapter.

12. The disposable polymer-structure filtering kit as recited in claim 1, wherein the vacuum take-off adapter is configured to seal with the funnel.

* * * * *